United States Patent
Lu et al.

(10) Patent No.: US 9,228,984 B2
(45) Date of Patent: Jan. 5, 2016

(54) GAS CHROMATOGRAPHY-MASS SPECTROMETRY METHOD AND GAS CHROMATOGRAPHY-MASS SPECTROMETRY APPARATUS THEREFOR HAVING A CAPTURE AND RELEASE DEVICE

(76) Inventors: Hongliang Lu, Xiamen (CN); Kai Lin, Xiamen (CN); Jing Yu, Xiamen (CN); Qun Chen, Xiamen (CN)

(*) Notice: Subject to any disclaimer, the term of this patent is extended or adjusted under 35 U.S.C. 154(b) by 0 days.

(21) Appl. No.: 13/609,290

(22) Filed: Sep. 11, 2012

(65) Prior Publication Data
US 2013/0126719 A1      May 23, 2013

(30) Foreign Application Priority Data
Nov. 23, 2011 (CN) .......................... 2011 1 0378211

(51) Int. Cl.
*H01J 49/26* (2006.01)
*G01N 30/46* (2006.01)
*G01N 30/72* (2006.01)

(52) U.S. Cl.
CPC .......... *G01N 30/461* (2013.01); *G01N 30/7206* (2013.01)

(58) Field of Classification Search
CPC ....................................................... H01J 49/26
USPC ....................................................... 250/282
See application file for complete search history.

(56) References Cited

U.S. PATENT DOCUMENTS

| 3,518,059 | A | * | 6/1970 | Levy ............................. 436/158 |
| 5,196,039 | A | * | 3/1993 | Phillips et al. ................ 210/656 |
| 5,492,555 | A | * | 2/1996 | Strunk et al. ..................... 95/86 |
| 6,311,544 | B1 | * | 11/2001 | Bertrand ..................... 73/23.35 |

FOREIGN PATENT DOCUMENTS

| CN | 201803991 U | 4/2011 |
| CN | 201837615 U | 5/2011 |

* cited by examiner

*Primary Examiner* — Phillip A Johnston
(74) *Attorney, Agent, or Firm* — David and Raymond Patent Firm

(57) ABSTRACT

A GC-MS method is provided with installing a sample injector; installing a heart-cutting unit; installing a first capillary column; connecting a switching valve to the heart-cutting unit; installing a capture and release device to the heart-cutting unit; connecting the capture and release device to the switching valve; connecting the switching valve to an MS; rotating the switching valve to either connect the first and second interconnecting columns, or connect the second capillary column and the second interconnecting column; injecting the sample gas into the first capillary column; by setting a time slot and carrier gas pressure of the heart-cutting unit, while causing fractions of simple compounds to be cut out and travel to the MS, causing fractions of complex compounds to be cut out; after the simple compounds finished in MS, causing complex compounds to be released from the capture and release device; and sending the compounds.

3 Claims, 2 Drawing Sheets

GAS CHROMATOGRAPHY-MASS SPECTROMETRY METHOD AND GAS CHROMATOGRAPHY-MASS SPECTROMETRY APPARATUS THEREFOR HAVING A CAPTURE AND RELEASE DEVICE

BACKGROUND OF THE INVENTION

1. Field of the Invention

The invention relates to gas chromatography-mass spectrometry (GC-MS) instrument and more particularly to a GC-MS method and a GC-MS apparatus therefor, the GC-MS apparatus having a capture and release device.

2. Description of Related Art

A conventional gas chromatography-mass spectrometry (GC-MS) apparatus is shown in FIG. 1 and comprises a sample injector 1, a heart-cutting unit 3 for separating gaseous compounds carried by carrier gas from the sample injector 1 into different fractions, a first capillary column 2 interconnecting the sample injector 1 and the heart-cutting unit 3, a flame ionization detector (FID) 7, an interconnecting column 4 interconnecting the FID 7 and the heart-cutting unit 3, a mass spectrometer (MS) 6, and a second capillary column 5 interconnecting the heart-cutting unit 3 and the MS 6. The FID 7 can be replaced with nitrogen-phosphorous detector (NPD) or one of similar detectors.

However, a number of drawbacks have been found in the conventional GC-MS apparatus. In detail, as sample gaseous compounds are preliminarily separated by the first capillary column 2 into different fractions, through setting different time slot and carrier gas pressure of the heart-cutting unit 3, the simple compounds with good separation separated by the first capillary column 2 are to be sent to a detector such as FID or NPD via the interconnecting column 4 for analysis while the complex compounds which are not separated from each other completely and cannot be further separated from each other by the first capillary column 2, are required to be sent to the second capillary column 5, which are of different solid phase from that of the first capillary column 2, for further separation before being sent to the MS 6 for quantitative and qualitative analysis. The simple compounds detected by the detector FID or NPD from a conventional GC-MS can only be able to be resulted in a quantitative analysis while no qualitative analysis as regards the name, structure, CAS No., etc. of such simple compounds may be concluded, thus causing inconvenience to the user. That is, different fractions cannot be sent to the MS 6 at the same time for analysis. Adding another MS to the GC-MS device can solve the problem but it will increase cost. Further, relevant software is required for control purposes.

Thus, the need for improvement still exists.

SUMMARY OF THE INVENTION

It is therefore one object of the invention to provide a method of operating a capture and release device with a switching valve to a gas chromatography-mass spectrometry comprising the steps of: installing a sample injector; installing a heart-cutting unit downstream of the sample injector; installing a first capillary column to connect the sample injector and the heart-cutting unit; connecting a switching valve downstream to the heart-cutting unit via a first interconnecting column; installing a capture and release device downstream to the heart-cutting unit, the capture and release device being able to capture the elution co-eluted from the heart-cutting unit via a cooling unit as well as release the elution via a heating unit; connecting the capture and release device to the switching valve via a second capillary column; connecting the switching valve to a mass spectrometer (MS) via a second interconnecting column; rotating the switching valve to either (a) connect the first and second interconnecting columns, or (b) connect the second capillary column and the second interconnecting column; injecting the sample gas into the first capillary column for preliminary separation via the sample injector; by setting a time slot and carrier gas pressure of the heart-cutting unit, while causing fractions of simple compounds to be cut out and travel to the MS via the first interconnecting column, the switching valve and the second interconnecting column to result in a quantitative and qualitative analysis, causing fractions of complex compounds to be cut out and travel to the capture and release device to be captured via a cooling unit; after the analysis for the simple compounds is finished in MS, causing complex compounds to be released from the capture and release device via a heating unit and travel to the second capillary column for further separation; sending the compounds from the second capillary column to the MS for analysis via the valve and the second interconnecting column to result in a quantitative and qualitative analysis.

The above and other objects, features and advantages of the invention will become apparent from the following detailed description taken with the accompanying drawings.

DETAILED DESCRIPTION OF THE INVENTION

Figure 1:
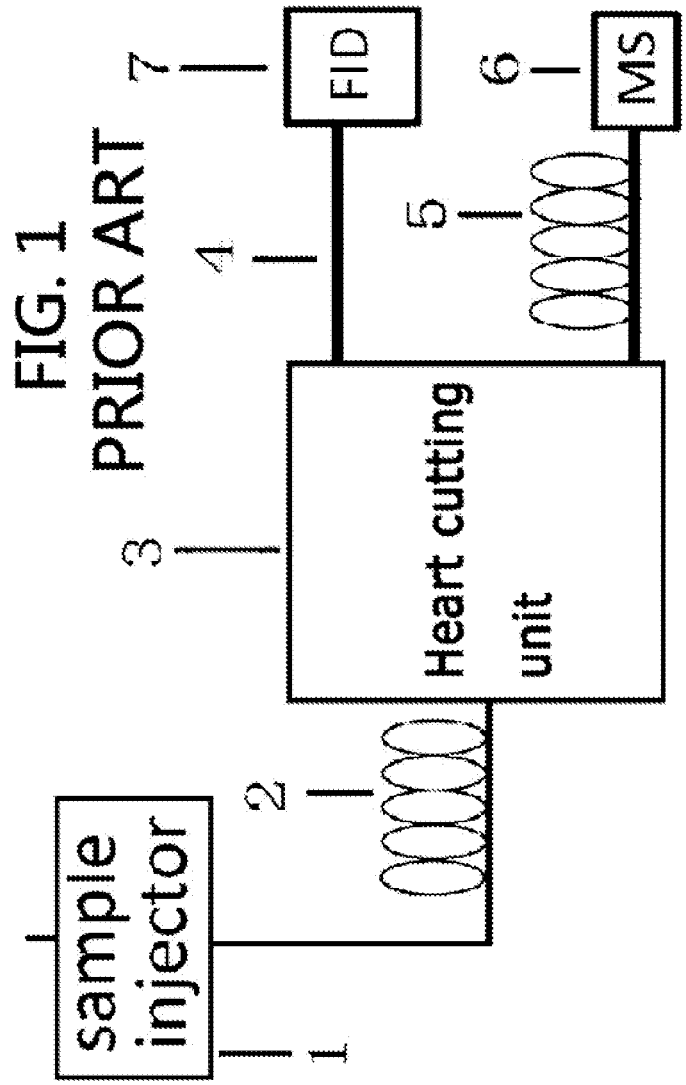
FIG. 1 is a schematic diagram of a conventional GC-MS apparatus.
Figure 2:
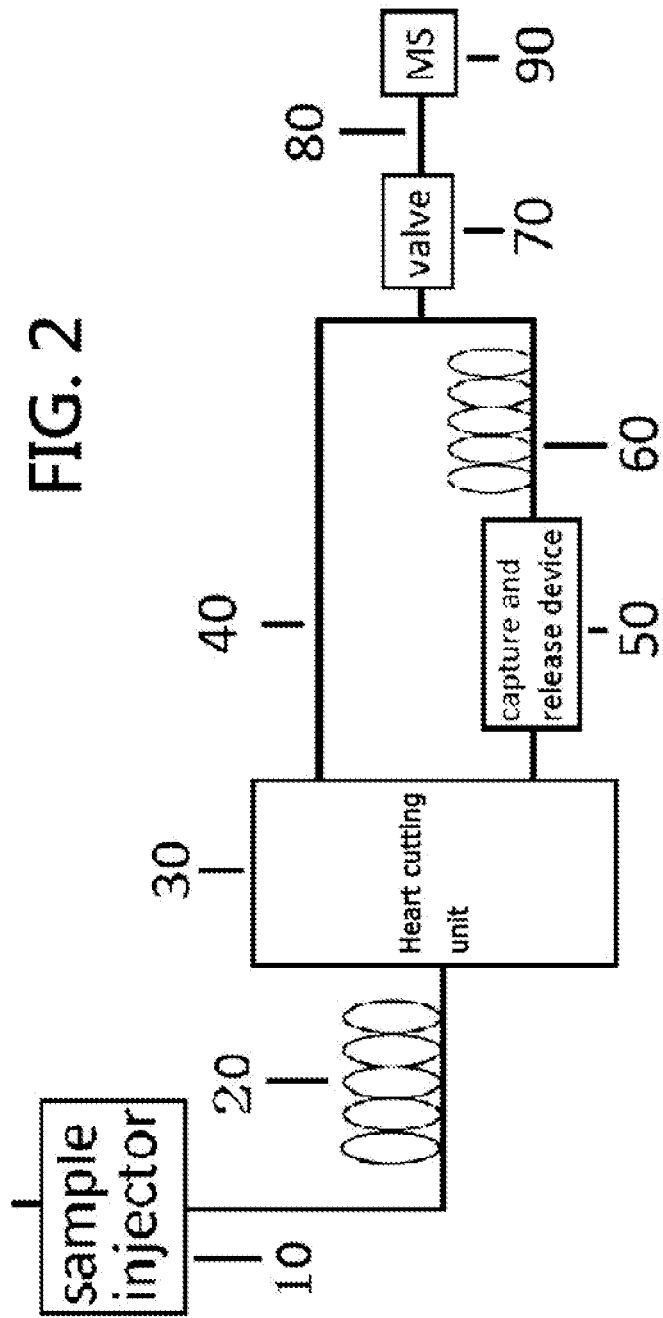
FIG. 2 is a schematic diagram of a GC-MS apparatus according to the invention.

Referring to FIG. 2, a GC-MS apparatus equipped with a capture and release device with a switching device in accordance with the invention comprises the following components as discussed in detail below.

A sample injector 10 is provided to allow carrier gas to pass through to carry chemical compounds. A heart-cutting unit 30 is provided downstream of the sample injector 10 to cut the gaseous compounds carried by the carrier gas from the sample injector 10 into different fractions. A first capillary column 20 is installed to connect the sample injector 10 and the heart-cutting unit 30. A first interconnecting column 40 interconnects a switching valve 70 and the heart-cutting unit 30. A second capillary column 60 is provided downstream of the heart-cutting unit 30. A capture and release device 50 is provided downstream the heart-cutting unit 30 and at an inlet of the second capillary column 60 for capturing and releasing compounds leaving the heart-cutting unit 30, the capture and release device 50 being able to capture the elution co-eluted from the heart-cutting unit 30 via a cooling unit as well as release the elution via a heating unit. The second capillary column 60 interconnects the capture and release device 50 and the switching valve 70. The switching valve 70 can either be rotated to (a) connect the first interconnecting column 40 and the second interconnecting column 80 or (b) connect the second capillary column 60 and the second interconnecting column 80. A second interconnecting column 80 interconnects the valve 70 and a mass spectrometer (MS) 90.

It is noted that compounds in both the first interconnecting column 40 and the second capillary column 60 after separation can be sent to the same MS 90 for analysis via the switching valve 70.

The capture and release device 50 may employ liquid nitrogen, liquid carbon dioxide, liquid ammonia, and Freon for capturing compounds separated from the heart-cutting unit 30. Alternatively, the capture and release device 50 may employ liquid nitrogen, liquid carbon dioxide, liquid ammonia, and Freon for cooling the carrier gas (e.g., helium or nitrogen) which in turn is used to capture the compounds. Still alternatively, an electronic capture device can also be employed to cool the carrier gas in addition to its capture function.

Subsequently, the capture and release device 50 may directly or indirectly heat air, nitrogen, helium or other gas which in turn is used to quickly release the captured compounds. Alternatively, an electronic heating device cans also be employed to quickly release the captured compounds in addition to its heating function.

The capture and release device 50 may perform a single capture or a plurality of captures of the compounds separated from the heart-cutting unit 30. The separated compounds are next sent to one or more capillary columns for further separation. It is noted that capture and separation are done sequentially not simultaneously by the capture and release device 50. Time for capture and time for release can be set independently.

GC-MS method of the invention is illustrated by the following three embodiments:

Embodiment I

First, sample chemical compounds are carried through the sample injector 10 by carrier gas prior to be sent into the first capillary column 20 for preliminary separation; by setting a time slot and carrier gas pressure of the heart-cutting unit 30, while causing fractions of simple compounds cut from the heart-cutting unit 30 to travel to the MS 90 via the first interconnecting column 40, the switching valve 70 and the second interconnecting column 80 to result in a quantitative and qualitative analysis, fractions of complex compounds cut from the heart-cutting unit 30 are sent to the capture and release device 50 to be captured via a cooling unit. Liquid nitrogen employed by the capture and release device 50 as cooling medium cools gaseous nitrogen which is in turn sprayed onto the capture unit of the capture and release device 50. The capture unit of the capture and release device 50 thus captures the complex compounds cut from the heart-cutting unit 30. After the analysis for the simple compounds is finished in MS 90, by activating an electric heater, the air, gaseous helium or other gas in the release unit of the capture and release device 50 may be heated to release the captured compounds into the second capillary column 60 for further separation. Time for capture or release can be set as desired. Finally, rotate the switching valve 70 to connect the second capillary column 60 and the second interconnecting column 80 so that compounds from the second capillary column are sent to the MS via the second interconnecting column 80 to result in a quantitative and qualitative analysis In detail, simple compounds (i.e., non capture being required) which are distinctively separated by the first capillary column 20 are directly sent to the MS 90 for analysis via the first interconnecting column 40, the switching valve 70 and the second interconnecting column 80.

Secondly, the capture unit of the capture and release device 50 is activated to capture the compounds cut from the heart-cutting unit 30.

After the MS 90 finishes analyzing the compounds sent from the first capillary column 20, the release unit of the capture and release device 50 is activated to blow the heated air, gaseous nitrogen, gaseous helium, or other gas to carry the compounds through the second capillary column 60 for further separation. The further separated compounds from the second capillary column 60 are finally sent to the MS 90 via the valve 70 and the second interconnecting column 80 for analysis.

Embodiment II

First, sample chemical compounds are carried through the sample injector 10 by carrier gas prior to be sent into the first capillary column 20 for preliminary separation; by setting a time slot and carrier gas pressure of the heart-cutting unit 30, while causing fractions of simple compounds cut from the heart-cutting unit 30 to travel to the MS 90 via the first interconnecting column 40, the switching valve 70 and the second interconnecting column 80 to result in a quantitative and qualitative analysis, fractions of complex compounds cut from the heart-cutting unit 30 are sent to the capture and release device 50 to be captured via a cooling unit. Liquid nitrogen employed by the capture and release device 50 as cooling medium surrounds and cools the capture unit. The capture unit of the capture and release device 50 thus captures the complex compounds cut from the heart-cutting unit 30. After the analysis for the simple compounds is finished in MS 90, by activating an electric heater, the air, gaseous helium or other gas in the release unit of the capture and release device 50 may be heated to release the captured compounds into the second capillary column 60 for further separation. Time for capture or release can be set as desired. Finally, rotate the switching valve 70 to connect the second capillary column 60 and the second interconnecting column 80 so that compounds from the second capillary column are sent to the MS via the second interconnecting column 80 to result in a quantitative and qualitative analysis In detail, simple compounds (i.e., non capture being required) which are distinctively separated by the first capillary column 20 are directly sent to the MS 90 for analysis via the first interconnecting column 40, the switching valve 70 and the second interconnecting column 80.

Secondly, the capture unit of the capture and release device 50 is activated to capture the compounds cut from the heart-cutting unit 30.

After the MS 90 finishes analyzing the compounds sent from the first capillary column 20, the release unit of the capture and release device 50 is activated to blow the heated air, gaseous nitrogen, gaseous helium, or other gas to carry the compounds through the second capillary column 60 for further separation. The further separated compounds from the second capillary column 60 are finally sent to the MS 90 via the valve 70 and the second interconnecting column 80 for analysis.

Embodiment III

First, sample chemical compounds are carried through the sample injector 10 by carrier gas prior to be sent into the first capillary column 20 for preliminary separation; by setting a time slot and carrier gas pressure of the heart-cutting unit 30, while causing fractions of simple compounds cut from the heart-cutting unit 30 to travel to the MS 90 via the first interconnecting column 40, the switching valve 70 and the second interconnecting column 80 to result in a quantitative and qualitative analysis, fractions of complex compounds cut from the heart-cutting unit 30 are sent to the capture and release device 50 to be captured via a cooling unit. Liquid nitrogen employed by the capture and release device 50 as cooling medium cools gaseous nitrogen which is in turn sprayed onto the capture unit of the capture and release device 50. The capture unit of the capture and release device 50 thus captures the complex compounds cut from the heart-cutting unit 30. After the analysis for the simple compounds is finished in MS 90, the release unit, which is a heater, of the capture and release device 50 is heated to release the captured compounds into the second capillary column 60 for further separation. Time for capture or release can be set as desired. Finally, rotate the switching valve 70 to connect the second capillary column 60 and the second interconnecting column 80 so that compounds from the second capillary column are sent to the MS via the second interconnecting column 80 to result in a quantitative and qualitative analysis In detail, simple compounds (i.e., non capture being required) which are distinctively separated by the first capillary column 20 are directly sent to the MS 90 for analysis via the first interconnecting column 40, the switching valve 70 and the second interconnecting column 80.

Secondly, the capture unit of the capture and release device 50 is activated to capture the compounds cut from the heart-cutting unit 30.

After the MS 90 finishes analyzing the compounds sent from the first capillary column 20, the release unit of the capture and release device 50 is heated to release the compounds into the second capillary column 60 for further separation. The further separated compounds from the second capillary column 60 are finally sent to the MS 90 via the valve 70 and the second interconnecting column 80 for analysis.

While the invention has been described in terms of preferred embodiments, those skilled in the art will recognize that the invention can be practiced with modifications within the spirit and scope of the appended claims.

What is claimed is:

1. A gas chromatography-mass spectrometry method comprising the steps of:
   (1) installing a sample injector;
   (2) installing a heart-cutting unit downstream of the sample injector;
   (3) installing a first capillary column to connect the heart-cutting unit and the sample injector;
   (4) connecting a valve to the heart-cutting unit via a first interconnecting column;
   (5) connecting the valve to the heart-cutting unit via a second capillary column, wherein the heart-cutting unit connects both of the first interconnecting column and the second capillary column to the first capillary column;
   (6) providing a capture and release device downstream the heart-cutting unit at an inlet of the second capillary column;
   (7) connecting the valve to a mass spectrometer (MS) via a second interconnecting column, wherein the first interconnecting column and the second capillary are respectively connected between the heart-cutting unit and the valve, wherein the valve connects both the first interconnecting column and the second capillary to the mass spectrometer via the second interconnecting column;
   (8) carrying chemical compounds through the sample injector by carrier gas;
   (9) carrying the compounds from the sample injector to the first capillary column for preliminary separation
   (10) by setting a time slot and carrier gas pressure of the heart-cutting unit, preliminarily separated compounds from the first capillary column are cut by the heart-cutting unit into simple compounds and complex compounds
   (11) while sending the simple compounds to the MS for analysis via the first interconnecting column, the valve, and the second interconnecting column, causing the capture and release device to capture the complex compounds;
   (12) after the analysis for the simple compounds is finished in the MS, causing the second capillary column to further separate the complex compounds leaving the capture and release device; and
   (13) sending the compounds separated from the second capillary column to the MS for analysis via the valve and the second interconnecting column.

2. A gas chromatography-mass spectrometry system, comprising:
   a sample injector for injecting chemical compounds carried by carrier gas;
   a first capillary column connected to the sample injector for preliminarily separating the chemical compounds;
   a heart-cutting unit connected to the first capillary column for cutting the preliminarily separated compounds from the first capillary column into simple compounds and complex compounds;
   a first interconnecting column connected downstream to the heart-cutting unit;
   a second capillary column, which is connected downstream to the heart-cutting unit, has an inlet;
   a capture and release device provided downstream of the heart-cutting unit at the inlet of the second capillary column;
   a valve connected downstream to both the first interconnecting column and the second capillary column;
   a second interconnecting column connected to the valve; and
   a mass spectrometer connected to the second interconnecting column, wherein when the simple compounds are sent to the mass spectrometer for analysis via the first interconnecting column, the valve, and the second interconnecting column, the capture and release device is arranged to capture and retain the complex compounds in the second capillary column, wherein after the analysis for the simple compounds is finished in the mass spectrometer, the capture and release device releases the complex compounds, and the second capillary column further separates the complex compounds, and then compounds separated from the second capillary column are sent to the mass spectrometer for analysis via the valve and the second interconnecting column.

3. A gas chromatography-mass spectrometry method, wherein a gas chromatography-mass spectrometry (GC-MS) apparatus comprises:
   a sample injector, a first capillary column, a heart-cutting unit, a first interconnecting column, a capture and release device, a second capillary column, a valve, a second interconnecting column, and a mass spectrometer, wherein said GC-MS apparatus comprises no flame ionization detector;
   wherein said heart-cutting unit connected downstream to said sample injector via said first capillary column, wherein said valve is connected downstream to said heart-cutting unit via said first interconnecting column, wherein said capture and release device is connected downstream to said heart-cutting unit and is connected to said valve via said second capillary column, wherein said valve is connected to said mass spectrometer (MS) via said second interconnecting column;
   wherein the method comprises the steps of:
   (1) installing said sample injector;

(2) installing said heart-cutting unit downstream to said sample injector;
(3) installing said first capillary column to connect said heart-cutting unit and said sample injector;
(4) connecting said valve downstream to said heart-cutting unit via said first interconnecting column;
(5) connecting said capture and release device downstream to said heart-cutting unit;
(6) connecting said capture and release device to said valve via said second capillary column;
(7) connecting said valve to said mass spectrometer (MS) via said second interconnecting column;
(8) carrying chemical compounds through said sample injector by carrier gas;
(9) carrying the compounds from said sample injector to said first capillary column for preliminary separation
(10) by setting a time slot and carrier gas pressure of said heart-cutting unit, preliminarily separated compounds from said first capillary column are cut by said heart-cutting unit into simple compounds and complex compounds
(11) while sending said simple compounds to said MS for analysis via said first interconnecting column, said valve, and said second interconnecting column, causing said capture and release device to capture said complex compounds;
(12) after the analysis for said simple compounds is finished in said MS, causing said second capillary column to further separate the complex compounds leaving said capture and release device; and
(13) sending the compounds separated from said second capillary column to said MS for analysis via said valve and said second interconnecting column;
wherein said valve is rotated to connect one of (i) said first interconnecting column and said second interconnecting column, and (ii) said second capillary column and said second interconnecting column.

* * * * *